United States Patent [19]

Brown, Jr. et al.

[11] Patent Number: 4,524,778
[45] Date of Patent: Jun. 25, 1985

[54] SKIN TEMPERATURE INDICATING AND RECORDING DEVICE

[75] Inventors: George T. Brown, Jr., Dayton; Lewis E. Blakely, Jr., Kettering, both of Ohio

[73] Assignee: American Thermometer Co., Inc., Dayton, Ohio

[21] Appl. No.: 509,933

[22] Filed: Jul. 1, 1983

[51] Int. Cl.³ .............................................. A61B 6/10
[52] U.S. Cl. .................................................... 128/736
[58] Field of Search ................ 128/736; 374/124, 137, 374/162, 158, 208, 207, 210; 434/88

[56] References Cited

U.S. PATENT DOCUMENTS

| | | | |
|---|---|---|---|
| 1,583,061 | 5/1926 | Loughridge | 434/88 |
| 3,847,139 | 11/1974 | Flam | 128/736 |
| 3,889,397 | 6/1975 | Flood | 434/88 |
| 4,064,872 | 12/1977 | Caplan | 128/736 X |
| 4,070,912 | 1/1978 | McNaughtan et al. | 128/736 X |
| 4,135,497 | 1/1979 | Meyers et al. | 128/736 |
| 4,327,742 | 5/1982 | Meyers et al. | 128/736 |
| 4,433,637 | 2/1984 | Buirley et al. | 128/736 X |

FOREIGN PATENT DOCUMENTS 2060879  5/1981  United Kingdom .............. 122/736

Primary Examiner—Edward M. Coven
Attorney, Agent, or Firm—Jacox & Meckstroth

[57] ABSTRACT

A method is disclosed for recording topological thermal data by scribing onto a thermographic indicator overlay thermograms produced by a thermochromatic band composed of temperature responsive liquid crystalline materials and temperature gradients of the thermograms determined with a surface thermometer having a plurality of display areas composed of thermochromatic compositions each exhibiting a distinct temperature event range spaced from the others by a temperature interval. Such method is especially adapted for application to the surface of the human body for the early detection of carcinomas as evinced by elevated temperature areas.

8 Claims, 6 Drawing Figures

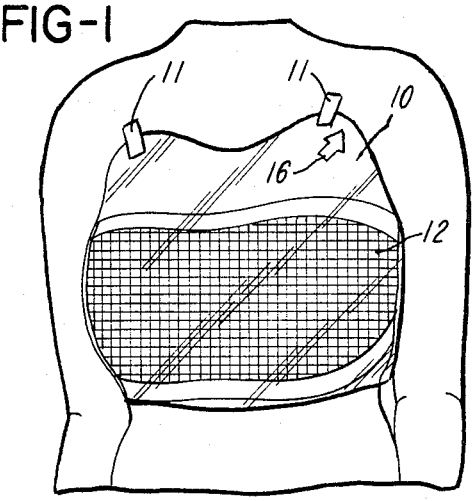
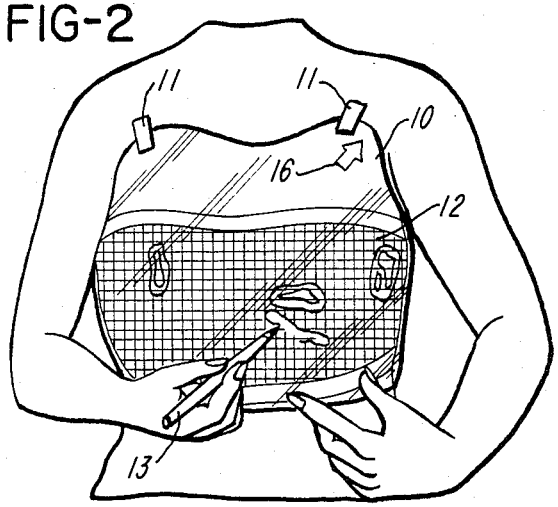
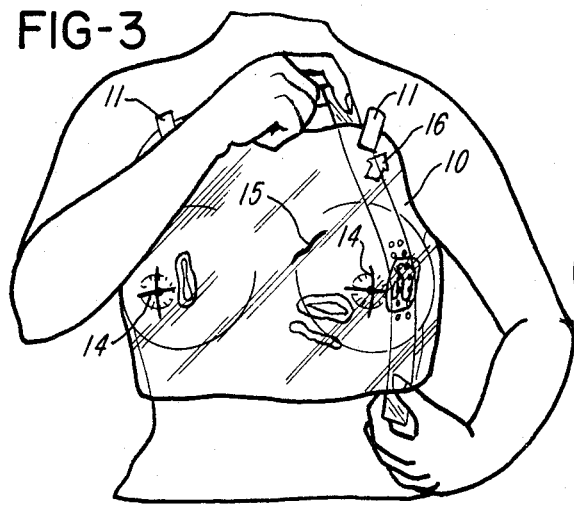
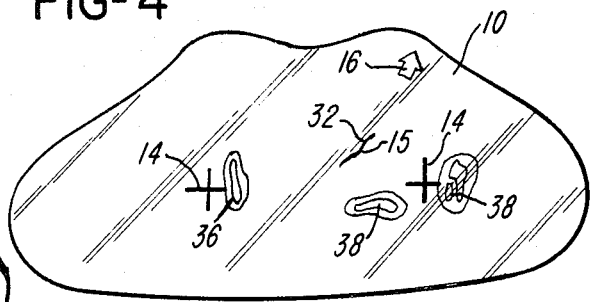
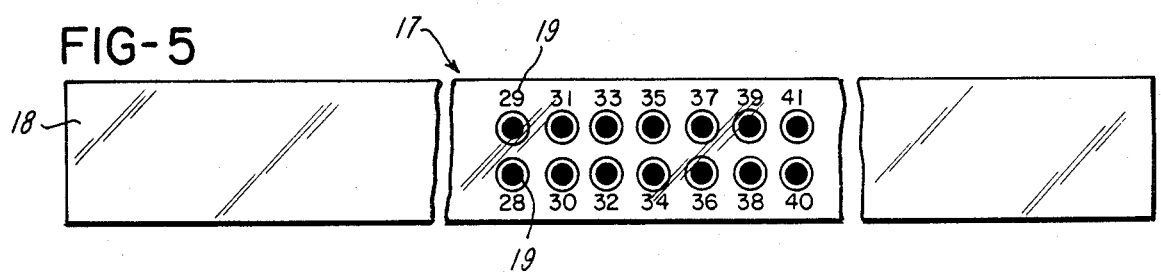
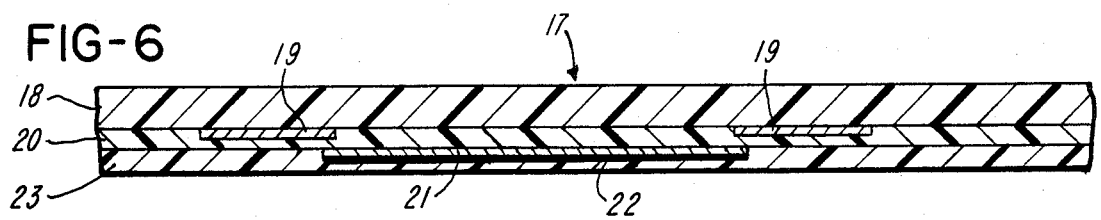

SKIN TEMPERATURE INDICATING AND RECORDING DEVICE

CROSS-REFERENCE TO RELATED APPLICATION

The thermographic indicator overlay disclosed in the present application was developed for use with thermographic scanning devices containing chromatically responsive liquid crystalline materials such as described in the application of George T. Brown, Jr., et al., Ser. No. 404,506, filed Aug. 2, 1982.

BACKGROUND OF THE INVENTION

1. Field of the Invention

This invention relates to a thermographic indicator overlay for use with thermographic scanning devices for recording topological thermal data.

2. Description of the Prior Art

The use of thermographic scanning devices employing chromatically responsive liquid crystalline materials for visual detection of body heat changes, for example, within the breasts of female humans to trigger further examination toward the early detection of breast cancer is known to the art as demonstrated by U.S. Patents Numbered U.S. Pat. No. 3,847,139 to Flam and U.S. Pat. No. 4,060,654 to Quenneville. Because the incipiency of malignant tumors is often accompanied by slight increases in the temperature of the tissue at the point of their development and such temperature increases are transmitted to the skin as hot spots, even before growths are palpable or otherwise identifiable, thermographic scanning is coming to be recognized as one of the preferred methods of early detection, especially of the fast-growing cancers, which is generally critical to a reasonable prognosis for cure or remission. The fullest exploitation of this great diagnostic potential obviously requires that these devices be regularly used on an ongoing basis normally at a monthly frequency, but more often under special circumstances; and this in turn requires that such use be performable by non professionals, preferably the patients themselves, without the need for special skills or training, for costly, cumbersome or complicated equipment or for extensive environmental controls.

In response to the relatively demanding thermal requirements, prior art thermographic scanning devices employ a plurality of distinct liquid crystalline systems applied to a like number of plates sequentially applied to the test area and photographically recorded. This requires complicated and expensive plate handling and storage equipment as well as a carefully calibrated system involving orientation photographic apparatus, all requiring the operating performance of a skilled and well trained practitioner. Consequently, the use of such devices is confined to hospitals or medical clinics; and the usage with any degree of frequency on an ongoing basis by the general public has not been possible.

In order to provide a thermographic scanning device that non professionals can use the present inventors disclosed in the Cross-Reference to Related Application, supra, a thermographic indicator having an array of chromatically responsive liquid crystals coated onto a flexible web-like substrate. Although such thermographic indicator provides a reusable device for the detection of topological thermal differentials, it does not provide an easy and inexpensive method for the recordation and storage of thermographic data.

SUMMARY OF THE INVENTION

This invention provides a thermographic indicator overlay to be used in combination with thermographic scanning devices that have an array of liquid crystalline materials coated onto a flexible web-like substrate. After the scanning device is positioned in direct contact to the body area to be examined, the outermost portion of the transparent overlay, which overlay is areally larger than the scanning device, is adhesively affixed directly to the body. The user traces on the overlay the contour of the hottest areas of the underlying thermograms with a marker such as a permanent felt-tipped pen. With the scanning device removed but with the overlay still in place, the user can then measure specific hot areas with a strip-type thermometer and record the data directly above and onto the overlay. For subsequent comparative thermal data analysis the user must mark the overlay for registration and orientation purposes. For example, for a breast scan the nipples are marked as they are distinguishable features, as are a scar, a mole or the like, and the location carefully marked onto the overlay as related to the right or the left breast. Comparative thermal data analysis may then be effectuated by stacking in registration a chronological series of overlays.

It is therefore an object of the present invention to provide a thermographic indicator overlay to be used with a thermographic scanning device capable of providing a record of a high resolution thermographic display of a small temperature change occuring at any point within a relatively broad temperature range.

It is a further object of the invention to provide a thermographic indicator overlay to be used with a thermographic scanning device adapatable for use in the early detection of cancer or of other contralateral heat differentials in the body due to various conditions of disease or to monitor chemotherapy or progress of surgical recovery.

Still another object of the invention is to provide a thermographic indicator overlay to be used with a thermographic scanning device which is so designed and constructed that such thermographic indicator overlay may be easily and conveniently used by non professionals or persons without special training or skills and without complicated or expensive equipment or support apparatus or carefully controlled environmental conditions.

Yet another object of the invention is to provide a method whereby thermographic data can be conveniently and permanently recorded in registration onto thermographic indicator overlays for comparative thermal analysis over long periods of time and at very low cost.

Achievement of the above and other objects and advantages which will be apparent from a reading of the following disclosure and the overcoming of the shortcomings and disadvantages of the prior art devices have proceeded in the case of the present invention from the discovery by Brown et al. as described in the Cross-Reference to Related Application, supra, that good resolution in the form of precise and readily distinguishable chromatic changes in response to relatively small temperature changes over a relatively broad temperature range may be achieved by the use of a specially designed and constructed liquid crystalline system coated on a thin, planar flexible, dimensionally stable substrate to be held in contact with an area of surface to be tested.

BRIEF DESCRIPTION OF THE DRAWINGS

FIG. 1 is a perspective view of a thermographic indicator overlay positioned over a thermographic indicator combined to form a breast scanning detector and recorder according to the invention as they are being used on the fragmentarily shown human body. The overlay is adhesively taped to the user's body and an orientation arrow appears at user's upper left arm.

FIG. 2 is a perspective view similar to FIG. 1 except the thermograms that appear on the thermographic indicator are traced by the user with a felt-tipped pen on the transparent overlay.

FIG. 3 is a perspective view similar to FIG. 1 except the thermographic indicator has been removed and the user has positioned a strip thermometer of the invention under the thermogram marked on the overlay. Marked on the overlay by the user are two crosses showing the location of the nipples and a wavy line showing the location of a scar.

FIG. 4 is a planar view of the overlay shown in FIG. 3 removed from the body of the user. Temperature readings of the thermograms and the scar are marked on the overlay.

FIG. 5 is a planar view of a strip thermometer according to the invention.

FIG. 6 is an enlarged, fragmentary, cross sectional view of the strip thermometer according to the invention shown in FIG. 5.

DETAILED DESCRIPTION OF THE PREFERRED EMBODIMENTS

The thermographic indicator overlay web 10 as shown in FIGS. 1-4 is a relatively thin flexible film preferably of plastic material which is tear resistant and transparent. Suitable films include polyvinyl chloride, polyolefins such as polyethylene or polypropylene, polyethylene terephthalate, polyvinylidene chloride, polyvinyl chloride copolymer, polyurethane and the like, preferably polypropylene. Depending upon the particular film selected, the thickness of the film is typically in the range of 1.0 mil to 3.0 mils, preferably 2.0 mils in the case of polypropylene.

Overlay web 10 is adhered to the body by a label or an adhesive patch 11 on the topmost edge along or above the collarbone area. This is above the area where a thermographic indicator or breast scanning band 12 is positioned so that the breast scanning band 12 can be easily adjusted for better observations while overlay web 10 remains fixed in position to the breasts. After breast scanning band 12 has been in contact with the user's body for a short period of time, chromatic thermograms as shown in FIG. 2 appear and the edges of the thermal last color to appear in the hottest areas are traced by the user using a black permanent ink felt-tipped pen 13. Breast scanning band 12 is removed and a pair of intersecting lines 14 and a body scar 15 are marked with pen 13 as is a directional arrow 16 if it is not preprinted on overlay web 10. Surface thermometer 17 is inserted under overlay web 10 and is manipulated by the user in order to read the highest temperature of each thermogram and the distinguishable body marking such as scar 15 and likewise marked on overlay web 10 with pen 13. FIG. 4 exemplifies the temperature response of three thermograms and a control.

The detailed construction of the surface thermometer 17 is shown in FIGS. 5 and 6 wherein web 18 is a relatively thin flexible film preferably of plastic material which is tear resistant, moisture proof, transparent, and whose surface is or can be made to be receptive to the various compositional layers of this invention. Suitable films include polyvinyl chloride, polyolefins such as polyethylene or polypropylene, polyethylene terephthalate, polyvinylidene chloride, polyvinyl chloride copolymer, polyurethane and the like, preferably polyethylene terephthalate. Depending upon the particular film selected, the thickness of the film is typically in the range of 2.0 mils to 6.0 mils, preferably 4.0 mils in the case of polyethylene terephthalate. The length of the film is 14.0 inches to 18.0 inches and the width of film is 0.75 inch to 1.0 inch.

In the preferred embodiment of the invention on one broadside surface of web 18 a mask 19 comprising the indicia, alphanumerical information and configurational patterns, is applied by one or more of the conventional printing methods notably gravure, lithography, letterpress or silkscreen using a conventional ink suitable to the particular method of printing. The ink used to print alphanumerical information and configurational patterns may be black, white or color. Alphanumerical information consists of numerical temperature readings of the adjacent temperature responsive elements, company logo, and instructional information whereas configurational patterns comprise a geometrical figure that frames the temperature responsive elements such as a circle, square, triangle, or the like, preferably a circle. The use of configurational patterns enhances the visibility of the temperature responsive elements when they respond to a particular temperature.

A subcoating 20, which is next applied by one of the conventional printing or coating methods, compatibly adheres to the surface of the oleophillic mask 19 and to the web 17 whose untreated surface is also oleophillic. The subcoating provides a surface that is receptive to the subsequently applied aqueous coatings. In addition to serving as a means whereby oleophobic material is bonded to materials that are oleophillic, the subcoating 20 greatly decreases delamination effects particularly noticeable along the edges of such film interfaces. The principal material of subcoating 20 is an acrylic ester copolymer supplied by Rohm and Haas Company under the trade designation Rhoplex N-495. In order to decrease the deleterious effects caused by ultraviolet radiation upon the temperature responsive elements, an ultraviolet radiation stabilizer is added to the subcoating. A list of such compounds is disclosed in U.S. Pat. No. 3,656,909.

A coating 21 of temperature responsive elements of micro-capsules comprises liquid crystalline cholesteric esters encased in capsule walls which are themselves composed of a gelatinous substance such as gelatin chosen to have index of refraction substantially equivalent to that of the encased liquid crystalline cholesteric esters. Such encapsulated liquid crystalline esters 2-50 microns in diameter, hereinafter ELC, are formed and composed as described in U.S. Pat. No. 3,920,574 to Brown et al. to which reference is hereby made for a detailed description thereof. By varying the formulation and construction of the ELC material according to practices well known to the art, the "event" or the temperatures which activate the color responses of the ELC may be predesigned, both as to the temperature at which a particular chromatic phenomenon occurs and as to the range of temperatures over which the entire spectrum of such phenomena is spread. Thus, a particular "event" type of ELC may be so formulated that it will refract light going from red/tan, through green and blue starting at a particular design temperature, e.g. 20° C., and continuing through a range of increased temperatures.

In one specific arrangement of ELC event types in a surface thermometer 17 according to the invention and embodying the above teachings, a plurality of ELC display areas are positioned adjacent to numerical readings indicating the temperature of the particular display area. The color spectrum of each ELC is responsive to a different specific temperature range. Surface thermometer 17 contains a multiplicity of display areas from 28° C. to 40° C. with each area indicating a 1° C. increase of temperature.

Table I presents examples of two formulations, A and B, that illustrate the use of cholesteryl pelargonate (CP) with cholesteryl chloride (CCl) and cholesteryl isostearyl carbonate (CIC) and cholesteryl pelargonate (CP) with cholesteryl propionate (CPr) and cholesteryl oleyl carbonate (COC) to produce the thermochromatic responsive elements of the surface thermometer 17. The wt % of the esters of Table I are shown at 28° C. and 40° C. with the incremental 1° C. intervening temperatures being essentially a linear function of the quantity of esters used at the two aforesaid extremes of temperature. The wt % of the esters shown in Table I to produce a specific temperature are approximate and can vary somewhat because of batch to batch differences inherent in the manufacture of such complex materials. Surprisingly CCl is essentially interchangeable with CPr as CIC is with COC with only subtle differences noticeable in the choice of esters. For example, CCl in formulation A produces thermochromatic response elements having a more pronounced blue event (longer tail) than does CPr in formulation B.

TABLE I

| Formulation | | Temperature | |
|---|---|---|---|
| A | B | 28° C. | 40° C. |
| Wt. % CP | Wt. % CP | 53.0 | 68.9 |
| Wt. % CCl | Wt. % CPr | 3.9 | 2.9 |
| Wt. % CIC | Wt. % COC | 43.1 | 28.2 |

In order to produce an optically integrated assemblage of temperature sensitive microspheres, onto subcoating 20 a slurry in the form of an aqueous dispersion of twenty-five (25%) solids consisting of a mixture of substantailly equal parts of ELC and polyvinyl alcohol as a typical binder is then applied. This application may be by conventional coating processes or by droplet deposition from hollow needles to provide a wet coating thickness of the order of 0.02 inch which, upon drying at room temperature for eight hours or more under moderate humidity, will result in a dry coating thickness of approximately 0.005 inch. As indicated above the surface thermometer of this invention has a multiplicity of different display areas and for each particular display area a particular ELC is coated. It is to be noted that the polyvinyl alcohol or other hydrophillic binder such as gelatin, polyurethane or the like should have a refractive index substantially equivalent to that of the liquid crystal droplets as should the walls of the microcapsules in which they may be encapsulated. Other suitable binders for the supporting matrix are numerous and typically would include rubbers and elastomers, plastics, polyolefins, inonomers, resins and viscous materials of reasonable clarity and refractive match to the microcapsules.

Over the ELC layer a black opaque layer 22 is applied using the same coating methods that apply the ELC layer but unlike the ELC formulations that are applied to particular display areas the black opaque layer 22 may be applied either onto the particular ELC coated areas or it may be applied to entire area that defines the surface thermometer. The coating comprises a non-reflective ink so that all or most of the ambient light striking the detection surface will be absorbed by such coating and the only light visible to a viewer will be that reflected or refracted by the ELC. A composition containing a light absorbing material such as carbon black dispersed in the materials of the subcoating disclosed above is preferred.

In a preferred embodiment of this invention a thin cleanable polymeric layer 23 is applied over black opaque layer 22 by using one of the previously cited conventional coating methods to provide a protective and cleanable film layer for the undercoated materials. Any of the previously cited polymeric materials can be used with polyethylene terephthalate being preferred.

In an alternate embodiment of this invention one broadside surface of web 18 is subjected to an electrostatic corona discharge from a high voltage source such as is used in electrostatically charging photoconductors in conventional electrophotography in order to convert an hydrophobic surface to a hydrophillic surface. The resulting charged web is rendered sufficiently receptive to the aqueous dispersion of ELC that subcoating 20 may be eliminated.

While the within invention has been described as required by law in connection with certain preferred embodiments thereof, it is to be understood that the foregoing particularization and detail have been for the purposes of description and illustration only and do not in any way limit the scope of the invention as it is more precisely defined in the subjoined claims.

What is claimed is:

1. A device for sensing and recording the skin surface temperature in selected areas of a human body, comprising a first flexible panel of film-like material, said first panel having a width sufficient to extend across the chest of the body for covering and contacting both breast of the body and for conforming to the curvature of the breast, a coating of temperature responsive liquid crystalline marterials carried by said first flexible panel and effective to produce a thermogram of the skin surface in the area of both breast in thermal contact with said first panel, a second flexible panel of transparent plastics film material directly overlying said first panel and contacting said first panel, said second panel also having a width sufficient to extend across the chest of the body, the thermogram on said first panel being visually observable through said second panel in contact with said first panel, marker means for recording on said second panel a selected pattern detail of the underlying thermogram on said first panel in contact with said second panel, means for attaching said second panel to the body in the area to be examined, means for supporting said first panel between the skin surface and said second panel, said latter supporting means providing for removing said first panel without removing said second panel, an elongated flexible thermometer band adapted to be positioned between the skin surface and said second panel after said first panel is removed, and said thermometer band having opposite end portions projecting above and below said second panel to facilitate gripping said thermometer band and precisely positioning said thermometer band between the skin surface and said second panel whereby temperatures from the thermometer band can be recorded on the second panel.

2. A device as defined in claim 1 wherein said second panel has an upper edge portion projecting above said first panel, and adhesive means for attaching said upper edge portion to the skin surface to facilitate removing said first panel without removing said second panel.

3. A device as defined in claim 1 wherein the temperature responsive liquid crystal materials contain about 53.0–69.0 weight percent cholesteryl pelargonate, 3.0–4.0 weight percent cholesteryl chloride, and 28.0–43.0 weight percent cholesteryl isostearyl carbonate.

4. A device as defined in claim 1 wherein the temperature responsive liquid crystal materials contain about 53.0–69.0 weight percent cholesteryl pelargonate, 3.0–4.0 weight percent cholesteryl propionate, and 28.0–43.0 weight percent cholesteryl oleyl carbonate.

5. A device as defined in claim 1 wherein the second panel is larger than the first panel and has an edge portion projecting above the first panel to facilitate attaching the second panel to the skin surface and removing the first panel.

6. A device as defined in claim 1 wherein the first panel comprises a film of polyethylene terephthalate polyester.

7. A device as defined in claim 1 wherein the thermometer band includes an array of temperature responsive liquid crystal compositions each having a distinct temperature range.

8. A device as defined in claim 7 wherein the compositions are arranged in a plurality of spaced zones, and the band has corresponding temperature indicating numbers for the zones.

* * * * *